June 27, 1972 R. A. HENSZ Plant Pat. 3,222
GRAPEFRUIT TREE
Filed Nov. 18, 1970
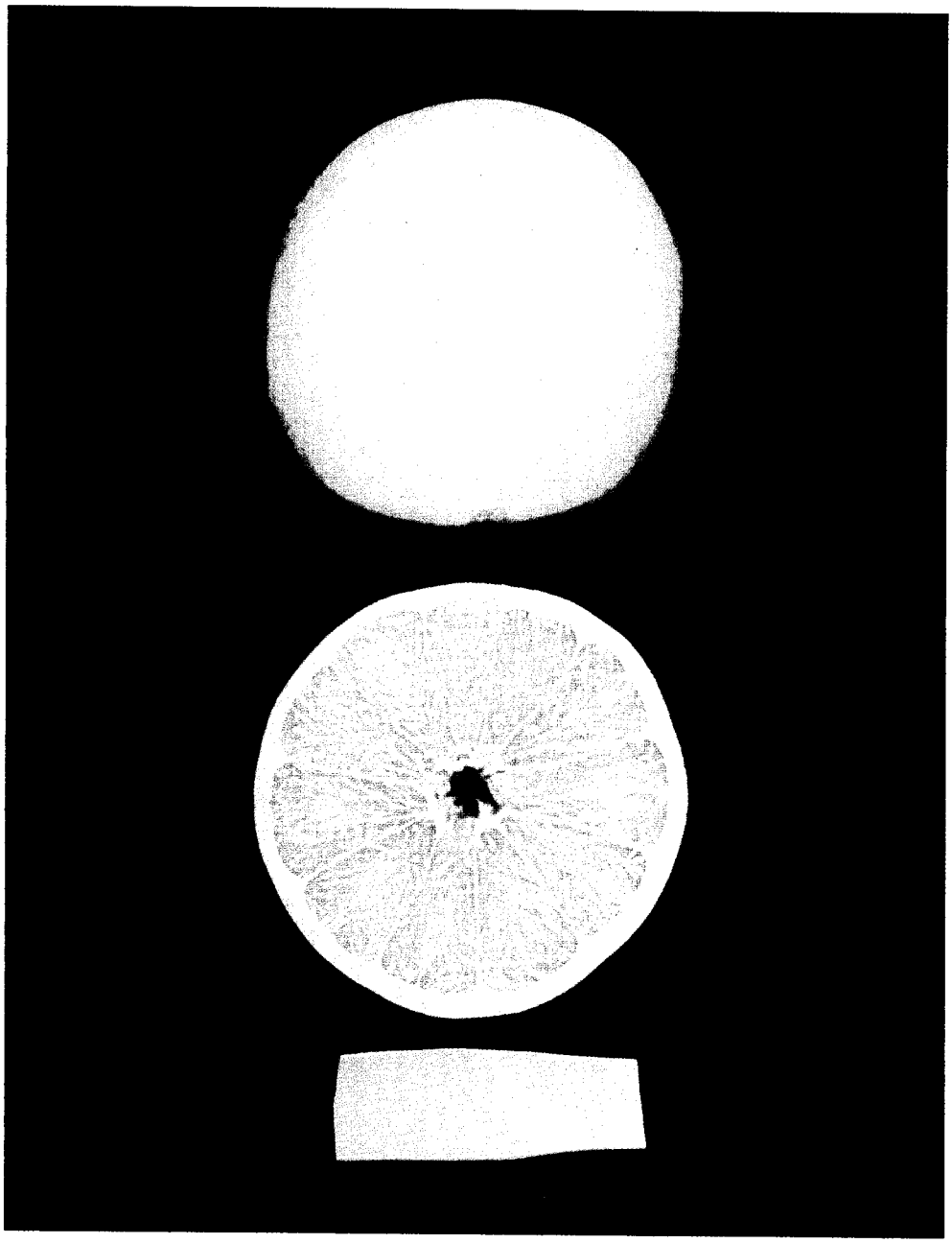
Richard A. Hensz
INVENTOR
BY Clarence A. O'Brien and Harvey B. Jacobson
Atty's United States Patent Office Plant Pat. 3,222
Patented June 27, 1972

3,222
GRAPEFRUIT TREE

Richard A. Hensz, Weslaco, Tex., assignor to Texas A & I University, Kingsville, Tex.

Filed Nov. 18, 1970, Ser. No. 90,883
Int. Cl. A01h 5/03
U.S. Cl. Plt.—45 1 Claim This present discovery pertains to a new and distinct variety of grapefruit tree that had its origin as a mutation of an entire seedling tree grown from seed of the little known variety, Hudson (unpatented), that had been irradiated with thermal neutrons in an atomic reactor. The irradiation treatment was performed by the Brookhaven National Laboratories, Long Island, N.Y. The seed was treated and planted by the applicant in the spring of 1959 at the Texas A & I University Citrus Center, Weslaco, Tex. In the summer of 1960, a bud was taken from the resulting seedlings and propagated on sour orange rootstock. This budded tree was planted in the field in the winter of 1961–62. Fruiting was first observed on this tree in 1967.

The fruit of the new variety is a seedless grapefruit whose yellow peel color has a reddish tint with areas of distinct red blushes. It has a deep red flesh color throughout the season that is approximately three times redder than the Henninger's Ruby Red (U.S. Plant Patent No. 53) grapefruit variety. It offers exceptional quality for the fresh market, sufficient pigmentation for processing a truly red juice, and has characteristics that would make it suitable for sectioning. It has an unusual red pigmentation in the cambium layer of the trunk and branches.

The distinctive fruit of the new variety is shown in the accompanying illustrations in which:

The illustration at the top is an exterior view of one of the fruit in the month of March.

The illustration in the middle is a transverse mid-section in a plane substantially perpendicular to the axis of the fruit in the month of March.

The illustration at the bottom is a strip of bark from the tree at the budunion with the section to the left the red pigmented claimed variety and the lower section colorless sour orange rootstock.

*Color*

Color of the fruit flesh varies slightly during the season, the flesh color being more intense earlier in the season. Colors of the fruit peel and flesh and the cambium of the tree are exemplified in the month of March as corresponding approximately to the following in "Maerz and Paul's Dictionary of Color" (1930).

Peel color: Calvary Deep Chrome (Plate 9, L–7) with blushes of Fire Red (Plate 1, F–12).
Flesh color: Poinsettia (Plate 2, L–9).
Cambium color on bark: Emberglow (Plate 3, G–10) to Burmese Gold + (Plate 3, C–11).

A distinctive feature of the tree is that the fruit is seedless (0–9, average 4) whereas, the fruit of the parent variety, Hudson, is very seedy (40–60).

The tree has borne crops for three seasons, the last of which it produced 3 boxes (over 240) fruit. The fruit was borne in all locations of the tree with no off-type fruit having been produced. The entire tree is true for the variety.

The new variety is distinct from the Burgandy (U.S. Plant Patent No. 1,276) in that the peel of the Burgandy is yellow and with no reddish tint nor are there any areas of red blushes on it. The albedo of the Burgandy is white, whereas, the albedo of this variety is red tinted. The Burgandy is out of the Thompson (unpatented) variety, and neither variety produces nucellar trees that bear pigmented fruit; thereas, the present variety is out of Hudson whose nucellar seedlings do produce trees whose fruit is pigmented.

Other characteristics of the new and distinct variety are:

*Fruit*

(1) Peel color is yellow with a reddish tint and has areas of distinct red blushes. The reddish peel color and blushes develop more intensely where the fruit is grown in a shaded area of the tree.

(2) Peel is smooth and thin. The oil glands are not raised.

(3) Peel color develops in late summer thus reducing the need for de-greening early fall-harvested fruit.

(4) Fruit size appears to be the same as present commercial red grapefruit varieties in Texas.

(5) Fruit shape is flattened to round and does not tend to sheepnose.

(6) The albedo is red tinted.

(7) The flesh retains a deep red color throughout the season that is approximately three times that of Henninger's Ruby Red grapefruit. Fruit sampled very late in the season (June 5) was found to contain 1.7412 mg. of lycopene per 100 gms. of flesh.

(8) Texture of the flesh is smooth and firm and is suited to sectioning.

(9) Segments number 10–13.

(10) Seeds number 0–9, average 4.

(11) Maturity is from October to May. Sugar and acid are both slightly higher than Henninger's Ruby Red. It has a distinct and delightful grapefruit flavor through the season.

*Tree*

(1) Has a unique and distinguishing characteristic in that the cambium layer of the tree branches and trunk is red. This character is also associated with the parent variety but is not found on other grapefruit varieties grown locally nor has it been reported in the literature.

(2) The original tree was grown from seed planted in 1959; therefore, it retains some juvenile vigor and would be expected to impart some juvenility to progeny trees.

(3) Shoot growth and internodes are somewhat shorter than other grapefruit varieties thus giving the appearance of a bushier compact tree. For that reason it may be of smaller stature than comparable trees of the same seedling age but equal to or larger than old-line trees.

(4) It should be free from citrus virus diseases because of its recent origin from seed. The Hudson variety is known to contain at least one citrus virus disease.

(5) Leaves are shaped as other grapefruit leaves with a broad petiole.

Having thus disclosed my invention, I claim:

1. The new and distinct variety of grapefruit tree characterized as to novelty by horticulturally seedless fruit with deep red flesh that stays through maturity, a yellow red-tinted peel with occasional red blushes, a reddish colored albedo, the fruit suited for fresh consumption and for process juice and sectioning, and having a red coloration in the cambium cells.

No references cited.

ROBERT E. BAGWILL, Primary Examiner

U.S. Cl. X.R.

48—1